United States Patent [19]

Lane et al.

[11] 4,139,627

[45] Feb. 13, 1979

[54] ANESTHETIC LOZENGES

[75] Inventors: Philip A. Lane; Bruce A. Brown, both of Brooklyn, N.Y.

[73] Assignee: Beecham Inc., Clifton, N.J.

[21] Appl. No.: 848,819

[22] Filed: Nov. 7, 1977

Related U.S. Application Data

[63] Continuation-in-part of Ser. No. 839,795, Oct. 6, 1977, abandoned.

[51] Int. Cl.$^2$ ..................... A61K 31/445; A61K 9/00; A61K 47/00
[52] U.S. Cl. ..................................... 424/267; 424/16; 424/361
[58] Field of Search ......................... 424/267, 16, 361; 429/267

[56] References Cited

U.S. PATENT DOCUMENTS

| | | | |
|---|---|---|---|
| 2,208,120 | 7/1940 | Coleman | 424/361 |
| 2,771,391 | 11/1956 | Bockstahuer | 424/267 |

OTHER PUBLICATIONS

PDR, 24th Ed., 1970, pp. 947-948.

*Primary Examiner*—Jerome D. Goldberg
*Attorney, Agent, or Firm*—Jacobs & Jacobs

[57] ABSTRACT

Anesthetic lozenges are prepared by combining an acid addition salt of 3-piperidino-p-alkoxypropiophenones-with a molten hard candy base with either the prior or simultaneous addition of a stabilizing amount of a pharmaceutically acceptable acid such as citric acid.

20 Claims, No Drawings

ANESTHETIC LOZENGES

This is a continuation-in-part of our co-pending application Ser. No. 839,795 filed Oct. 6, 1977, now abandoned.

The present invention is concerned with anesthetic lozenges.

3-Piperidino-p-alkoxypropiophenones wherein the alkoxy group contains from 2 to 8 carbon atoms and in particular the acid addition salts of these compounds are a known class of local anesthetic agents (see e.g. U.S. Pat. No. 2,771,391 and Profft, Chem. Tech. (Berlin) 4, 241 (1952). Two particularly useful members of this class are dyclonine hydrochloride which is 3-piperidino-4'-butoxypropiophenone hydrochloride and falicain which is 3-piperidino-4'-propoxypropiophenone hydrochloride. These compounds when topically applied, as for example in a 0.5% solution or a 1% cream, produce topical or local anesthetic effects. It is also known, however, that these compounds lack stability, particularly in aqueous media and the use of chlorobutanol has been proposed as a stabilizer for aqueous pharmaceutical preparations of dyclonine hydrochloride (see U.S. Pat. No. 2,868,689). It appears the same stability problems attach to falicain since the Merck Index indicates that aqueous solutions of this topical anesthetic should not be sterilized by autoclave methods.

Attempts to prepare a lozenge or trouche in which such compounds are mixed with a hard candy base demonstrated the existence of further stability problems. Hence while a compound such as dyclonine hydrochloride is stable up to about 150° C. (its melting point being 178° C.), a mixture with a conventional hard candy base results in degradation at temperatures as low as 120° C. In view of the documented lack of stability of this compound in aqueous media, it was postulated that a similar phenomenon occurred in the case of dyclonine hydrochloride and the molten hard candy base. Analytical studies employing UV and IR spectroscopy and thin layer chromatography demonstrated that the decomposition product formed in aqueous solutions of dyclonine hydrochloride was also present in lozenges.

More particularly, the present invention is based on the discovery that the degradation which occurs upon mixing a 3-piperidino-p-alkoxypropiophenone salt with a molten hard candy base can be minimized or eliminated through either the prior or simultaneous addition of an amount of a pharmaceutically acceptable acid to the molten hard candy base sufficient to stabilize said salt. Suitable acids include citric acid, fumaric acid, malic acid, tartaric acid, lactic acid, adipic acid and phosphoric acid. Citric acid is particularly useful.

The effect of citric acid on the thermal decomposition of dyclonine hydrochloride in molten hard candy base can be seen from the following:

Table 1

| Temperature | Dyclonine HCl | Candy Base | Citric Acid | % Recovery |
|---|---|---|---|---|
| 85° C | + | − | − | 104 |
| 85° C | + | + | − | 100 |
| 100° C | + | − | − | 104 |
| 100° C | + | + | − | 98 |
| 100° C | + | + | + | 103 |
| 105° C | + | + | − | 98 |
| 110° C | + | + | − | 91 |
| 120° C | + | − | − | 102 |
| 120° C | + | + | − | 69 |
| 120° C | + | + | − | 87 |
| 125° C | + | + | − | 71 |
| 125° C | + | + | + | 94 |
| 135° C | + | − | − | 99 |
| 135° C | + | + | − | 55 |
| 150° C | + | − | − | 102 |
| 150° C | + | + | − | 20 |
| 185° C* | + | − | − | 20 |

*Above melting point 178° C.

As can be seen from the above, dyclonine hydrochloride is itself stable up to about 150° C. but decomposes in the presence of molten candy base at about 120° C. The presence of citric acid, however, stabilizes the dyclonine hydrochloride at 125° C.

It appears that as little as 0.25% of citric acid will stabilize the dyclonine hydrochloride and molten candy base although superior stabilization is achieved utilizing levels of 0.5% citric acid. No significant increase in stabilization appears above 1% and therefore the amount of acid added in excess of this lower limit is not critical and is determined solely by economic considerations. The effect of various amounts of citric acid can be seen from Table 2 in which the recovery values of dyclonine hydrochloride which has been added to molten candy base at 135° C. is shown.

Table 2

| % Citric Acid | % Recovery |
|---|---|
| — | 62 |
| 0.25 | 86 |
| 0.50 | 96 |
| 0.75 | 93 |
| 1.0 | 96 |

Within the range of 105° C. to 135° C., which corresponds to temperatures encountered in actual process conditions, the effect of 1% citric acid on the recovery of dyclonine hydrochloride from a molten candy base can be seen in Table 3.

Table 3

| Temperature | Citric Acid (1%) | % Recovery |
|---|---|---|
| 105° C | No | 100 |
| 105° C | Yes | 96 |
| 115° C | No | 97 |
| 115° C | Yes | 100 |
| 125° C | No | 85 |
| 125° C | Yes | 97 |
| 135° C | No | 64 |
| 135° C | Yes | 96 |

In a large scale evaluation, four lots of dyclonine hydrochloride lozenges were prepared, one lot of which contained no citric acid and the remaining three of which contained 0.85% citric acid. For the three lots which did contain citric acid, the average percent recoveries were 105% (24 batches), 91.1% (22 batches), and 91.9% (19 batches). The average recovery for the lot which contained no citric acid was 75.2% (22 batches).

As noted above, the acid can be added to the molten candy mass prior to adding the anesthetic compound or can be intimately mixed with the active ingredient to form a homogeneous powder which is then added to the molten candy mass. Generally, the amount of topical anesthetic compound added will be such as to provide from about 0.025 to 1% by weight of the final lozenge. Preferably, the amount of topical anesthetic compound is 0.025–0.1%. A particularly preferred amount is 0.05%. The bulk of the lozenge will be composed of the hard candy base, serving as a carrier and of a conventional composition in the pharmaceutical art. In addition, flavoring agents such as menthol or methylsalicylate can be added, together with pharmaceutically acceptable colors and the like.

In a typical embodiment, the molten candy base is prepared in the conventional manner and transferred from the cooker to a transfer pan. The acid, for example citric acid, is added to the base prior to the addition of the dyclonine hydrochloride or simultaneously as a powdered mix. Any flavoring is added and the entire mixture is well blended. The candy mass is then transferred to a kneading table, mixed and lozenges formed.

Although 3-piperidino-p-n-butoxypropiophenone is the preferred topical anesthetic agent, the present invention is equally useful for other compounds of this class such as 3-piperidino-p-n-octyloxypropiophenone, 3-piperidino-p-n-ethoxypropiophenone, 3-piperidino-p-n-amoxypropiophenone, 3-piperidino-p-isobutoxypropiophenone, 3-piperidino-p-sec.-butoxypropiophenone, 3-piperidino-p-n-propoxypropiophenone, 3-piperidino-p-isoamoxypropiophenone, 3-piperidino-p-isopropoxypropiophenone, 3-piperidino-p-n-heptyloxypropiophenone and 3-piperidino-p-n-hexyloxypropiophenone.

Likewise, although the hydrochloride salt is preferred since it is readily available, other pharmaceutically acceptable salts of these piperidino compounds and falicain such as those formed with hydrobromic acid, fumaric acid, malic acid, tartaric acid, lactic acid, adipic acid, phosphoric acid, sulfuric acid, methane sulfonic acid, naphthene disulphonic, acetic acid and the like may also be utilized in a similar manner.

The resultant lozenge provides relief of pain and discomfort due to minor sore throats, minor mouth irritations, stomatitis and the pain and discomfort following periodontal procedures and minor oral surgery as a result of its anesthetic properties.

The following example illustrates a typical embodiment of the present invention.

The following non-limitative examples more particularly illustrate the present invention:

EXAMPLE 1

| Ingredient | Amount/Lozenge |
|---|---|
| 3-Piperidino-p-butoxypropiophenone HCl | 0.60 mg |
| Anhydrous Citric Acid | 20.40 mg |
| Flavor | 12.42 mg |
| Coloring Agent | 0.222 mg |
| Anhydrous Candy Base to | QS 2.40 gm |

The candy base is melted in a vacuum cooker and the coloring agent is added. The citric acid is next added and mixed well. The remaining ingredients are then added and the mixture poured on a kneading table, kneaded approximately seven minutes and lozenges then formed.

EXAMPLE 2

| Ingredient | Amount/Lozenge |
|---|---|
| 3-Piperidino-p-butoxypropiophenone HCl | 1.20 mg |
| Anhydrous Citric Acid | 20.40 mg |
| Flavoring | 12.42 mg |
| Coloring Agent | 0.222 mg |
| Anhydrous Candy Base to | QS 2.40 gm |

EXAMPLE 3

| Ingredient | Amount/Lozenge |
|---|---|
| 3-Piperidino-p-butoxypropiophenone HCl | 2.40 mg |
| Anhydrous Citric Acid | 20.40 mg |
| Flavoring | 12.42 mg |
| Coloring Agent | 0.222 mg |
| Anhydrous Candy Base to | QS 2.40 gm |

EXAMPLE 4

| Ingredient | Amount/Lozenge |
|---|---|
| 3-Piperidino-p-butoxypropiophenone HCl | 24.0 mg |
| Menthol USP | 6.62 mg |
| Coloring (green) | 0.222 mg |
| Flavoring | 5.8 mg |
| Anhydrous citric acid | 20.40 mg |
| Anhydrous candy base | QS to 2.4 gm |

What is claimed is:

1. A process for the production of a topical anesthetic lozenge which comprises heating a candy base suitable for said lozenges to the melting point, adding an amount of a pharmaceutically acceptable acid selected from the group consisting of citric acid, fumaric acid, malic acid, tartaric acid, lactic acid, adipic acid and phosphoric acid prior to or simultaneously with the addition of an anesthetically effective amount of a pharmaceutically acceptable acid addition salt of the compound of the formula

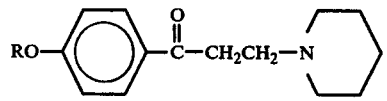

wherein R is alkyl of 2 to 8 carbon atoms, sufficient to stabilize said salt, said amount being from 0.2% to about 1.0% by weight of lozenge.

2. A process according to claim 1 wherein the acid is citric acid.

3. A process according to claim 1 wherein about 0.5% of citric acid is added.

4. A process according to claim 1 wherein about 0.75% of citric acid is added.

5. A process according to claim 1 wherein about 1.0% of citric acid is added.

6. A process according to claim 1 wherein said salt is the hydrochloride salt.

7. A process according to claim 1 wherein R is n-butyl.

8. A process according to claim 1 wherein R is n-propyl.

9. A process according to claim 1 wherein R is n-butyl and the salt is the hydrochloride salt.

10. A process according to claim 1 wherein R is n-butyl, the salt is the hydrochloride salt and the acid is citric acid.

11. A lozenge comprising an anesthetically effective amount of a pharmaceutically acceptable acid addition salt of the compound of the formula

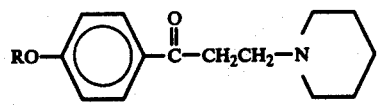

wherein R is alkyl of 2 to 8 carbon atoms, and an amount of a pharmaceutically acceptable acid selected from the group consisting of citric acid, fumaric acid, malic acid, tartaric acid, lactic acid, adipic acid and phosphoric acid sufficient to stabilize said salt intimately mixed in a hard candy base, said amount being from about 0.2% to about 1.0% by weight of lozenge.

12. A lozenge according to claim 11 wherein the acid is citric acid.

13. A lozenge according to claim 11 which contains 0.5% by weight of citric acid.

14. A lozenge according to claim 11 which contains 0.75% by weight of citric acid.

15. A lozenge according to claim 11 which contains 1.0% by weight of citric acid.

16. A lozenge according to claim 11 wherein the salt is the hydrochloride salt.

17. A lozenge according to claim 11 wherein R is n-butyl.

18. A lozenge according to claim 11 wherein R is n-propyl.

19. A lozenge according to claim 11 wherein R is n-butyl and the salt is the hydrochloride salt.

20. A lozenge according to claim 11 wherein R is n-butyl, the salt is the hydrochloride salt and the acid is citric acid.

* * * * *